United States Patent [19]
Kumomi et al.

[11] Patent Number: 5,970,361
[45] Date of Patent: Oct. 19, 1999

[54] PROCESS FOR PRODUCING SEMICONDUCTOR DEVICE HAVING POROUS REGIONS

[75] Inventors: Hideya Kumomi, Yokohama; Takao Yonehara, Atsugi; Nobuhiko Sato, Yokohama, all of Japan

[73] Assignee: Canon Kabushiki Kaisha, Tokyo, Japan

[21] Appl. No.: 08/846,501

[22] Filed: Apr. 28, 1997

Related U.S. Application Data

[62] Division of application No. 08/681,490, Jul. 23, 1996, abandoned, which is a continuation of application No. 08/386,347, Feb. 10, 1995, abandoned, which is a continuation of application No. 08/108,803, Aug. 19, 1993, abandoned.

[30]    Foreign Application Priority Data

Aug. 25, 1992    [JP]    Japan ................................ 4-247175

[51] Int. Cl.$^6$ .................................................. H01L 21/76
[52] U.S. Cl. ............................................ 438/409; 438/960
[58] Field of Search ................................... 257/613, 617, 257/103; 437/71, 170; 438/409, 960

[56]    References Cited

U.S. PATENT DOCUMENTS

| | | |
|---|---|---|
| 4,092,445 | 5/1978 | Tsuzuki et al. ............................ 427/85 |
| 4,096,619 | 6/1978 | Cook, Jr. . | |
| 4,393,577 | 7/1983 | Imai ........................................ 438/409 |
| 5,023,200 | 6/1991 | Blewer et al. . | |
| 5,139,624 | 8/1992 | Searson et al. ....................... 204/129.3 |
| 5,147,555 | 9/1992 | Brown et al. ............................ 210/698 |
| 5,156,706 | 10/1992 | Sephton ................................. 159/47.1 |
| 5,225,374 | 7/1993 | Fare et al. . | |
| 5,242,863 | 9/1993 | Xian-Zheng et al. . | |
| 5,250,460 | 10/1993 | Yamagata et al. ........................ 437/62 |
| 5,272,355 | 12/1993 | Namavar et al. .......................... 257/3 |

FOREIGN PATENT DOCUMENTS 57103243    6/1982    Japan .............................. H01J 29/45

OTHER PUBLICATIONS

Beale et al., "An Experimental and Theoretical Study of the Formation and Microstructure of Porous Silicon," Journal of Crystal Growth, vol. 73, pp. 622–663 (1985).

Xiang–Zheng Tu, "Fabrication of Silicon Microstructures Based on Selective Formation and Etching of Porous Silicon," Journal of Electrochemical Soc'y vol. 135, No. 8, pp. 2105–2107 (1988).

L.T. Canham, "Silicon Quantum Wire Array Fabrication by Electrochemical and Chemical Dissolution of Wafers," Applied Physics Letters, vol. 57, No. 10, pp. 1046–1048, (1990).

T. Unagami et al.; "Structure of Porous Silicon Layer and Heat Treatment Effect", J. of the Electrochemical Socitey, vol. 125, No.8, Aug. 1978, pp. 1339–1344.

Y.V. Mii, "Observation of Large oscillator Strengths for both 1→2 and 1→3 Intersubband Translations of Step Quantum Wells", Applied Physics Letters, vol. 56, No. 11, Mar. 12, 1990, pp. 1046–1048.

Deutscher et al., "Studies of the Dissolution of Geothermal Scale", Lawrence Livermore Laboratory, 1980.

*Primary Examiner*—Jey Tsai
*Attorney, Agent, or Firm*—Fitzpatrick, Cella, Harper & Scinto

[57]    ABSTRACT

Disclosed are a semiconductor device having a porous member as an active region, the porous member comprising a plurality of porous regions having different structures or compositions; and a process for producing a semiconductor device, comprising a step of modifying partially a non-porous substrate, and a subsequent step of making the substrate porous.

7 Claims, 3 Drawing Sheets

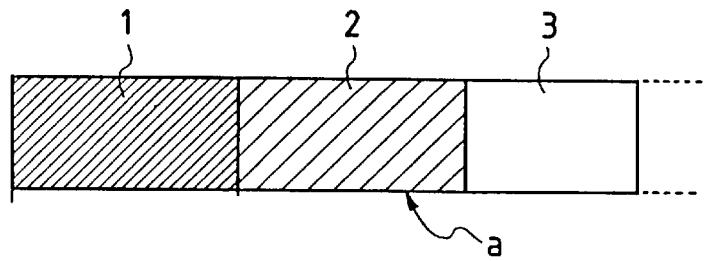
FIG. 1A
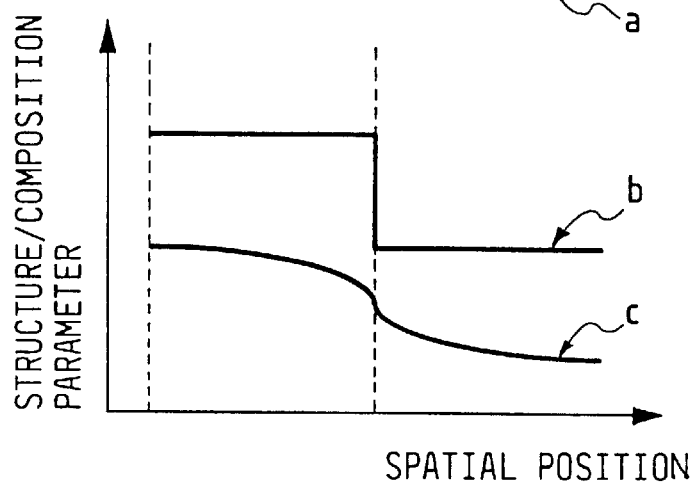
FIG. 1B
FIG. 2A
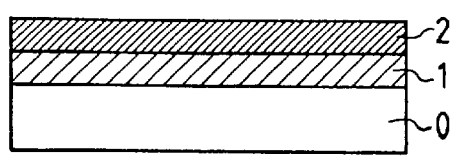
FIG. 2B
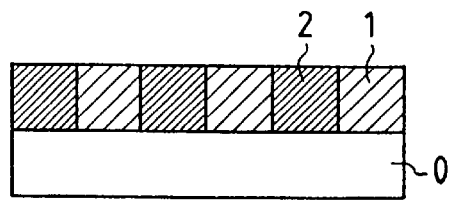

PROCESS FOR PRODUCING SEMICONDUCTOR DEVICE HAVING POROUS REGIONS

This application is a division, of application Ser. No. 08/681,490 filed Jul. 23, 1996, now abandoned, which is a continuation of application Ser. No. 08/386,347, filed Feb. 10, 1995, now abandoned, which is a continuation of application Ser. No. 08/108,803, filed Aug. 19, 1993, now abandoned.

BACKGROUND OF THE INVENTION

1. Field of the Invention

The present invention relates to a semiconductor device such as an electronic element, an optical element, and integrated circuit thereof which performs functions of light-emission, sensing, or the like, and also relates to a process for producing the semiconductor device. In particular, the present invention relates to a semiconductor device having a porous region and to a process for producing the device.

2. Related Background Art

Porous materials are attracting attention in recent years as a novel functional material for constituting an active region of an element.

The porous structure of a semiconductor crystal of Group IV, for example, were primarily used in the past as structural members which are not related to the electronic and optical properties of the material and uses such as formation of SOI (Silicon On Insulator) structure utilizing capability of high speed oxidation (see, for example, T. Unagami and M. Seki: J. Electrochem. Soc., 125, 1339 (1978)).

In recent years, the porous material is applied to an active region material of a gas sensor by utilizing the large surface area resulting from the porosity (see, for example, A. Motohashi, et al.: Oyo Butsuri Gakkai Gakujutsu Koenkai (Shuki) Yokoshu (Preprint of Autumnal Meeting of Society of Applied Physics), 29p-ZB-9 (1986)); and light-emission phenomenon was discovered which is caused by a structure sufficiently fine for imprisonment of carrier quantum (see L. T. Canham, Appl. Phys. Lett., 56, 1046 (1990)). Since then, studies are actively being made on functional application of porous material to light-emitting element, and other applications. The functional application of the porous material will possibly become an attractive novel technique if several practical problems are solved, because the porous structure can be formed readily by treating the base material.

The most serious of the problems in realization of the functional application of the porous material is the lack of stability of structure of the material.

The porous material, as understood from the name, inherently has many voids in the space where the material is to be filled. Therefore, the structural strength is unavoidably low in comparison with the base material. Further the absolute value of the strength naturally depends on the size, shape, density, and so forth of the remaining structure. A material of finer porous structure is generally more brittle than the one having a coarser structure. Accordingly, a coarse porous material is advantageous as far as desired functions are performed with the coarse structure. However, in application fields in which finer structure is required, the structural instability becomes a serious problem.

Referring again to the example of the aforementioned semiconductor crystal of Group IV, a finer structure is desired to obtain a larger surface area for higher sensitivity of a gas sensor; and visible light-emission is not achievable without a superfine structure of finer than several nanometers. In the latter application, to obtain shorter wavelength of emitted light, much more finer structure is required.

Practically, however, such a superfine porous material is extremely brittle, and will collapse immediately on touching. Therefore, it is extremely difficult to practicalize the instable material with a definite element size.

Another problem in functional application of a porous material is the difficulty of signal transmission between the porous active region and the outside.

The active element needs to transmit or receive signal or energy to or from the porous region. However, the porous structure or the composition of the intended porous material is frequently not suitable for the transmittance function. For example, the aforementioned light-emitting element involves the problem that an electrode formed for injecting carriers into the porous active region is insufficient in structural strength and further does not give sufficient injection efficiency because of excessively high contact resistance.

Generally, unsolved problems exist not only in transmission of signals and energies but also in simultaneous practice of a plurality of functions.

SUMMARY OF THE INVENTION

An object of the present invention is not only to improve a structural strength of a semiconductor device having fine porous regions but also to provide a semiconductor device having fine porous regions which is improved in signal-energy transmission ability of the fine porous regions.

Another object of the present invention is to provide a semiconductor device which performs a plurality of functions which cannot be achieved by a device having only one kind of porous region and to provide a process for producing the device.

BRIEF DESCRIPTION OF THE DRAWINGS

FIG. 1 is a schematic diagram showing an embodiment of a semiconductor device having a plurality of different porous regions of the present invention.

FIGS. 2A and 2B illustrate schematic sectional views showing an embodiment of element construction of a semiconductor device of the present invention.

DESCRIPTION OF THE PREFERRED EMBODIMENTS

Figure 3A:
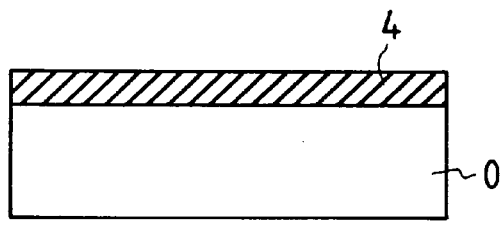
FIGS. 3A to 3F illustrate sectional views showing an embodiment of the process for producing a semiconductor device of the present invention.

The semiconductor device having a porous member as an active region of the present invention comprises a plurality of porous regions having different structures or compositions.

In one embodiment, the structure or composition changes discontinuously between the plurality of porous regions having different structures or compositions.

In another embodiment, the structure or composition changes continuously between the plurality of porous regions having different structures or compositions.

In still another embodiment, a porous region having a fine structure is supported by a porous region having a coarse structure.

The process for producing the semiconductor of the present invention comprises modifying partially a non-porous substrate, then making the substrate porous.

The another process for producing the semiconductor of the present invention comprises making a non-porous substrate porous by changing working conditions of porous structure formation.

The semiconductor device of the present invention has a plurality of porous regions having different structures or compositions. Some active regions may have a fine porous structure and perform a function of the main purpose, while other regions may have a coarse structure which has sufficient strength to support the aforementioned fine porous region structurally. Thereby the semiconductor device serves as a practical useful porous material without impairing the intended function.

Regions other than the main fine porous regions may be porous regions which have a structure and a composition showing a function and characteristics different from the main fine porous regions. Thereby, a semiconductor device is provided which has porous active elements having multiple functions without impairing the main object.

In the process for producing a semiconductor device of the present invention, a non-porous material is made porous by utilizing a material different from the non-porous material or by changing the working conditions. Thereby a semiconductor device is producible practicably which has a plurality of porous regions having different structures or compositions.

The embodiment of the semiconductor device and the process for producing it are described below in detail by reference to the drawings.

Structure of Semiconductor Device

Symbol "a" of FIG. 1 illustrates schematically the porous regions having different structures or compositions of a semiconductor device of the present invention. In symbol "a" of FIG. 1, the semiconductor device of the present invention comprises at least two porous regions 1, 2, 3, etc. having different structures or different compositions.

If the region 2 is the porous region having a fine structure of a composition which performs the intended function of the device, the region 1 has a structure or a composition which gives a sufficient structural strength. Thereby, the region 1 supports the region 2 to supplement insufficient structural strength of the region 2 and to make the element practicably stable. If the region 2 is the porous region having a fine structure or a composition which performs the intended function of the device and the region 1 is a porous region having a different function or characteristics from the region 2, then the device has the both functions or properties of regions 1 and 2 without impairing the main function of the region 2.

Symbols "b" and "c" of FIG. 1 show the difference between the regions 1 and 2 in terms of spatial change of parameters of the structure or composition. This change may be abrupt and discontinuous as shown in symbol "b" or otherwise may be gradual and continuous as shown in symbol "c". In the former case, the characteristics at the interface between the regions may be utilized as the function of the element. In the latter case, disadvantages caused by non-conformity between the regions may be reduced.

The region 3 and following regions including the region 3 may be a porous region which has a structure or composition different from that of the region 1 or 2, or the same structure or composition as that of the region 1 or 2. Otherwise, the region 3 and following regions may not be of the porous structure and may be a constituting region having high structural strength or having excellent signal-energy transmission ability with the exterior.

FIGS. 2A and 2B are schematic cross-sectional diagrams of a semiconductor device, showing more specifically an embodiment of the aforementioned concept of the element construction. FIG. 2A is a cross-sectional view of an example in which the porous regions having different structures or compositions are formed on a substrate in layers parallel to the substrate surface. FIG. 2B is a cross-sectional view of another example which has different porous regions partially on the substrate.

In FIGS. 2A and 2B, the porous regions are formed on a non-porous substrate 0 and are constructed from a porous regions 1 and 2 having a structure or composition different from each other.

If the porous region 1 is the active area which has a brittle structure and the porous region 2 has a strong structure, then the stability in structure of the entire element is achievable by either method of FIGS. 2A and 2B.

Even when direct transmission of signal or energy to the porous region 2 is difficult, the transmission can be practiced through the porous region 2 to the porous region 1 if the porous region 2 is capable of satisfactory transmission.

FIGS. 2A and 2B illustrate the case where two kinds of porous regions are involved. Naturally, additional different porous regions may coexist.

Process for Production

The formation of a plurality of porous regions according to the process for producing a semiconductor device according to the present invention is described regarding the element construction shown in FIGS. 2A and 2B.

Generally, in making a non-porous material porous by, for example, as etching, the spatial structure of the formed porous material depends largely on the structure and composition of the non-porous material or the working conditions. For example, in formation of porous silicon by anodization of crystalline silicon, the remaining structure of the porous silicon varies from several $\mu$m to several nm and the network structure of the porous matter varies greatly depending on the kind and the concentration of impurity in the crystalline silicon, the composition and concentration of the anodization solution, the electric current density of the anodization, and so forth.

Production Example 1

Figure 3B:
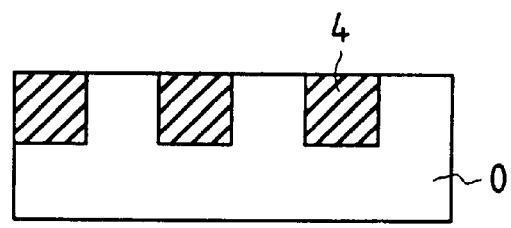

A region 4 having different structure or composition is formed initially on a non-porous substrate material 0 as shown in FIGS. 3A and 3B. This is conducted by local ion implantation or similar method to locally modify the substrate.

Figure 3C:
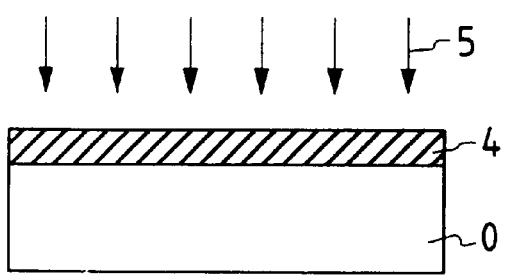
Figure 3D:
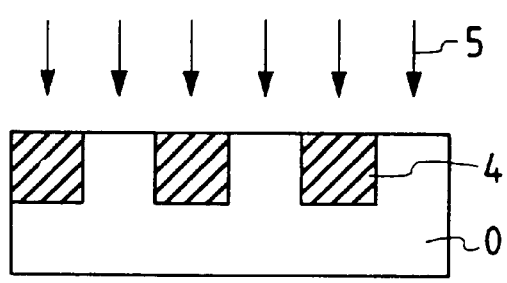
Figure 3E:
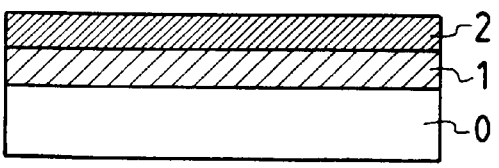
Figure 3F:
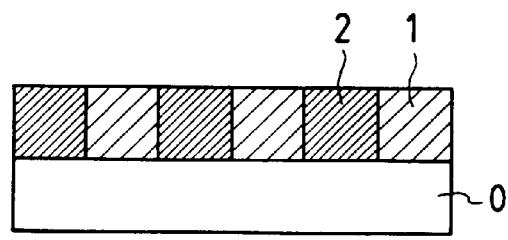

Subsequently, the substrate is subjected to working 5 from the surface of the substrate 0 for making the substrate porous (FIGS. 3C and 3D), the working for porosity including the aforementioned anodization. The regions having different structure or composition turn into porous regions 1 and 2 different in the structure or composition from each other even under the same conditions of working for porosity (FIGS. 3E and 3F). An element having a plurality of porous regions is produced in such a manner.

Production Example 2

A plurality of different kinds of porous regions can be formed by forming the regions by changing the working conditions for porous structure formation.

Figure 4A:
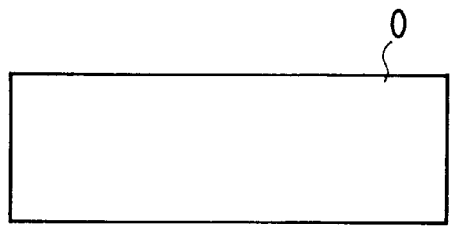
FIGS. 4A to 4F illustrate sectional views showing an embodiment of the process for producing a semiconductor device of the present invention.
Figure 4B:
Figure 4C:
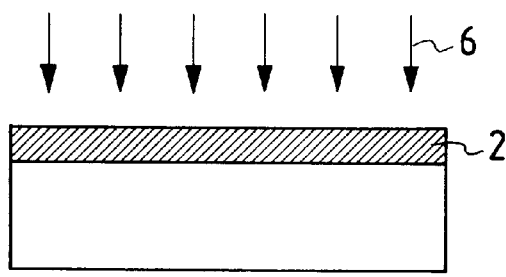
Figure 4D:
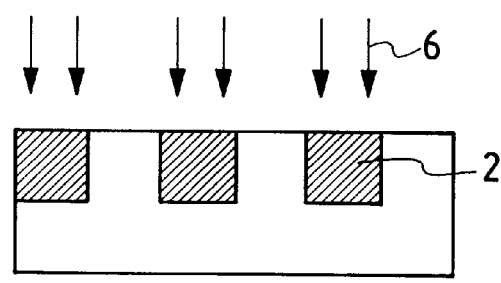
Figure 4E:
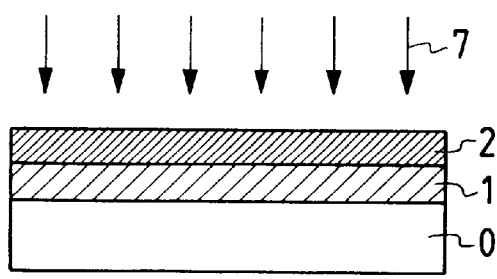
Figure 4F:
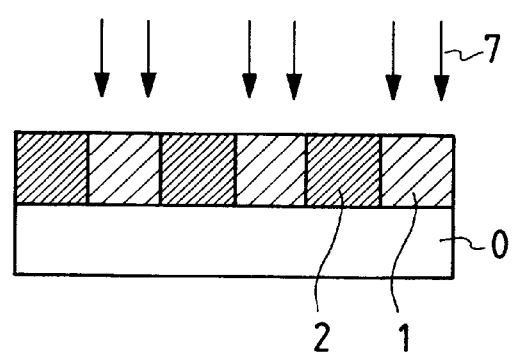

A process for realizing the element structures of FIGS. 2A and 2B is illustrated in FIGS. 4A to 4F. Non-porous material 0 having a uniform composition is employed (FIGS. 4A and 4B). The non-porous material is made porous by working under certain conditions A to form a porous region 2 (FIGS. 4C and 4D). To make the construction of FIGS. 4B, 4D and 4F, a protection measure has to be taken so as not to make porous the region other than the porous region 2. Specifically, patterning of a protection film, or a like measure is useful. Subsequently, the material is subjected to further porous structure formation working 7 under conditions B different from the conditions A (FIGS. 4E and 4F). Thereby, in the element construction (FIG. 4E), a further porous region 1 is formed additionally inside the porous region 2 with the porous region 2 kept unchanged. On the other hand, in element construction (FIG. 4F), a porous region 1 is formed in the region other than the porous region 2 if the porous region 2 is protected. If the porous region 1 may be formed directly below the porous region 2 in the construction (FIG. 4F), the protection of the region is not necessary.

In the case where a spatial modulation of working conditions is possible, the aforementioned protection and two-step working is not required, and steps of FIGS. 4D and 4F may be conducted simultaneously.

The change of the working conditions leads to a change at least in the structure or, in some cases, in the composition, of the formed porous material, thereby enabling to give different structures or compositions of the porous regions 1 and 2.

The processes for producing a semiconductor device of the present invention are described above by reference to FIGS. 3A to 3F and FIGS. 4A to 4F, in which the composition of the starting material for the porous material or the working conditions are changed respectively. Both methods may naturally be combinedly employed.

The above description is made regarding the production of elements having two kinds of porous regions. It is evident naturally that more than two kinds of layers of element structure can be formed in a similar process.

Further, the change of the structure or composition between the different porous regions may be selected readily to be discontinuous and abrupt, or continuous and gradual by controlling the spatial change of the preliminarily formed different structures or compositions, or controlling the time and spatial change of working conditions.

The construction of the element of the semiconductor device and the process for production thereof of the present invention are described more specifically by reference to typical examples.

EXAMPLE 1

A light-emitting element employing a porous silicon having an element structure of FIG. 2A was produced by the process shown in FIGS. 3A to 3F.

A monocrystalline silicon wafer of plane orientation [100] doped with boron having resistivity of 0.2 $\Omega \cdot$cm was used as the substrate and starting non-porous material. This wafer was oxidized by thermal oxidation to form $SiO_2$ layer of about 20 nm thick. Then phosphorus ions accelerated to 25 keV were implanted to the front face of the wafer at a dose of $7 \times 10^{13}$ cm$^{-2}$ by an ion implantation method. To the back face of the wafer, boron ions accelerated to 40 keV were implanted at a dose of $4 \times 10^{14}$ cm$^{-2}$. The implanted ions were activated by rapid thermal annealing in a nitrogen atmosphere at 1050° C. for one minute. Thereafter the $SiO_2$ layer was removed by using aqueous dilute hydrofluoric acid solution. The wafer was immersed in an aqueous 20 wt % hydrofluoric acid/ethanol solution between a pair of parallel plate platinum electrodes such that the portion other than the faces of the wafer was insulated. The electrode confronting the wafer front face was employed as the anode, and the wafer was anodized for 2 minutes by applying DC voltage between the platinum electrodes by controlling the current density constant at the wafer face at 10 mA$\cdot$cm$^{-2}$.

The surface of the resulting anodized silicon wafer was maintained in a mirror-polished state without formation of a crack or other defect, but the surface was observed to have discolored owing to the formation of porosity. The porosity formation was confirmed by observing a cross-section of a separately prepared sample with a high-resolution electron microscope. The anodization proceeded to the depth of about 3 $\mu$m from the surface of the wafer to form a porous layer. By more careful observation, the outermost thin layer of about 0.1 $\mu$m thick had a coarse structure of several hundred nanometers or more, while most of the region between the above-mentioned outermost thin layer and the interface with the non-porous portion of the silicon substrate contains a superfine structure of as small as several nanometers. The thin coarse-structure layer in the vicinity of the surface is considered to correspond to the surface layer which had become n-type by phosphorus ion implantation and annealing for activation practiced prior to the anodization. On the other hand, a wafer which was anodized without ion implantation at the surface had a uniform porous layer of a superfine structure and was brittle, so that the porous layer cracked soon after the anodization, or collapsed by slight touching.

After confirmation of sufficient stability of the porous layer of the wafer having been subjected to phosphorus ion implantation and anodization, an ITO film of 150 nm thick was formed on the surface of the wafer. The ITO film was patterned into several islands of 2 mm square. To each of the islands of ITO film, a lead-out electrode was provided by usual wiring technique of the IC process. Over the entire of the back face of the wafer, aluminum film of 400 nm thick was formed as the lower electrode.

With the element prepared above, DC current was made to flow between the electrodes on the both faces of the wafer. The element exhibited rectification characteristics to flow electric current with the back face electrodes employed as the anode, and emitted visible orange light with the threshold voltage of about 5 V. This light emission is considered to be due to electroluminescence caused by current injection into the superfine porous silicon layer through the junction interface between the coarse n-type porous layer and directly under p-type porous layer.

In this Example, of the two porous layers having different structure/composition, the thin coarse n-type porous layer on the front side of the wafer, with its structural strength, prevents collapse of the directly under superfine porous layer, and simultaneously functions as high efficient current-injecting layer for injecting current into the superfine porous layer on application voltage to the element. Thus the element structure having a plurality of porous regions play simultaneously two roles of maintaining both the function and structural strength and of performing a plurality of functions.

EXAMPLE 2

A gas sensor element employing a porous silicon having a structure of FIG. 2B was produced by the process shown in FIGS. 4B, 4D and 4F.

A monocrystalline silicon wafer of plane orientation [110] doped with boron having resistivity of 10 Ω·cm, and having been polished on both sides was used as the substrate and starting non-porous material. This wafer was oxidized by thermal oxidation to form $SiO_2$ layer of about 30 nm thick. On the back face of the wafer, photoresist was applied, and the applied photoresist was patterned by conventional lithography to leave resist pattern of 5 μm wide on 10 μm-square lattice lines. To the back face of the wafer, boron ions accelerated to 50 keV were implanted at a dose of $5 \times 10^{14}$ $cm^{-2}$. The resist was peeled off, and the wafer was subjected to annealing for activation in a nitrogen atmosphere at 950° C. for 30 minutes. Then the $SiO_2$ layer was removed by use of dilute hydrofluoric acid aqueous solution.

The wafer was anodized in the same manner as in Example 1 except for the hydrofluoric acid concentration of 25%, the current density of 5 mA·$cm^{-2}$, and the anodization time of 10 minutes.

In the wafer having been subjected to local ion injection like the one of this Example, the three-dimensional structure seemed to be maintained at least although significant change of color of the surface is exhibited and the surface is not in a mirror-polished state.

The cross-section of the wafer was observed by high-resolution electron microscopy. As the results, it was found that the porous layer had an average thickness of about 2.5 μm, the interface between the porous layer and the substrate silicon was not flat and projections and hollows were repeated gently at a cycle of about 10 μm, and the remaining structure of the porous layer changed from a coarse structure to a superfine structure continuously and synchronously with the projections and hollows. The periodical structure is assumed to be due to the two-dimensional distribution of the resistivity caused by local boron ion implantation at the back face of the wafer, and the corresponding spatial modulation of the electric current in the plane on the anodization. The structural strength of the entire porous layer is considered to be achieved by the coarse structure which supports mechanically the interposed superfine porous regions.

For comparison, a wafer was prepared which was implanted with ions uniformly on the back face without using resist pattern. This wafer began to collapse spontaneously at the porous surface immediately after washing and drying of the wafer, and the electron microscopical observation was not feasible.

Finally, after confirming the sufficient stability of the porous layer of the wafer surface, an aluminum electrode was deposited by mask vapor deposition in a thickness of 300 nm on the front face of the wafer, and aluminum film was formed in a thickness of 400 nm over the entire of the back face by sputtering.

The dependence of electric characteristics on the atmosphere around the element was investigated with the element formed between electrodes on the both faces of the wafer prepared in this Example. The electric capacity of the element was measured by varying the amount of vapor of water or alcohol in the air. In the both cases, the electric capacity of the element increased gradually with the amount of vapor with saturation tendency, which shows the function of the element as a gas sensor.

EXAMPLE 3

A light-emitting element employing a porous silicon having an element structure of FIG. 2A was produced by the process shown in FIGS. 4A, 4C and 4E.

A monocrystalline silicon wafer of plane orientation [111] doped with boron having resistivity of 1 Ω·cm was used as the substrate and starting non-porous material. On the entire of the back face of the wafer, an aluminum film of 400 nm thick was formed, and annealed in a hydrogen atmosphere at 400° C. for 30 minutes. Then, only the surface of the wafer was immersed in aqueous hydrofluoric acid/ethanol solution and the wafer was anodized by using the aluminum film of the back face as the cathode and an opposing platinum electrode as the anode. The hydrofluoric acid concentration of the etching solution was 35%, and the current density and the anodization time were varied successively in seven steps as shown in the Table below.

TABLE 1

| Step | Current density (mA · $cm^{-2}$) | Anodization time (minutes) |
|---|---|---|
| 1 | 0.5 | 20 |
| 2 | 5 | 4 |
| 3 | 10 | 2 |
| 4 | 5 | 4 |
| 5 | 15 | 1.5 |
| 6 | 5 | 4 |
| 7 | 20 | 1 |

The surface of the resulting anodized silicon surface was kept in a mirror-polished state without formation of a crack or other defect, but the surface was observed to have discolored owing to the formation of porosity. The cross-section of the sample was observed. As a result, the outermost surface layer of about 10 μm in a total thickness had a coarse structure and the under portion had a superfine porous structure. According to more careful observation, the superfine porous layer was composed of six layers, and the respective layers had slightly different structure from each other although the differences were not so significant as the difference between the outermost layer and the inner layer. Naturally, the differences of the structure among the layers are caused by the change of electric current density during the each porous layer formation.

After confirmation of the sufficient stability of the porous layer of the wafer surface, a thin gold film of 20 nm thick was deposited on the wafer surface by mask vapor-deposition.

With the element prepared above, DC current was made to flow between the electrodes on the front and back faces of the wafer. The element exhibited rectification characteristics to flow electric-current with the electrode on the back side employed as the anode, and emitted slightly warm-colored white visible light with the threshold voltage of about 10 V. This light emission is considered to be due to electroluminescence caused by current injection through the interface of gold of Schottky type junction into the superfine porous silicon layer.

The spectrum of the light emitted by the element showed that the light had a relatively flat emission strength over the range of from 500 nm to 800 nm or more. If the superfine porous silicon layer is formed under fixed conditions, the light emission spectra will distribute broadly and have a peak which tends to shift shorter wavelength corresponding to finer porous structure. Therefore, the white light emitted by the light-emitting element of this Example is considered to be due to the appropriate superposition of emission spectra of a plurality of porous layers having different size of structures.

As above, a plurality of the porous layers of the element coexist to perform a plurality of functions without impairing the functions of the respective layers, thereby achieving the second object of the present invention. Further, the first object of the present invention is simultaneously achieved in that the porous layer of the coarse structure at the outermost layer mechanically supports the layer of the under portion having a brittle superfine structure to achieve structural stability of the element.

EXAMPLE 4

A light-emitting element was prepared by employing porous silicon and silicon-germanium. A monocrystalline silicon wafer of plane orientation [100] doped with boron having resistivity of 10 Ω·cm prepared. To the back face of the wafer, boron ions accelerated to 40 keV were implanted at a dose of $4 \times 10^{14}$ cm$^{-2}$, and subjected to annealing for activation in an nitrogen atmosphere at 1000° C. for 10 minutes.

On the front face of the wafer, a multi-layered film having a quantum well structure of Si/SiGe was formed by low pressure CVD as follows. Initially a $Si_{0.95}Ge_{0.05}$ buffer layer of 300 nm thick was formed on the wafer. Then, formation of an $Si_{0.8}Ge_{0.2}$ layer of 5 nm thick and subsequent formation of an Si layer of 20 nm thick were repeated 20 times. Finally a boron-doped Si layer of 150 nm thick was formed thereon.

Over the entire of the back face, an aluminum film of 400 nm thick was formed, and was annealed in a hydrogen atmosphere at 400° C. for 30 minutes.

Subsequently, anodization was conducted in the same manner as in Example 3 except that the hydrofluoric acid of the etching solution was 45%, the electric current density was 20 mA·cm$^{-2}$, and the anodization time was 2 minutes.

The surface of the resulting anodized silicon wafer surface was kept in a mirror-polished state without formation of a crack or other defect, but the surface was observed to have discolored owing to the formation of porosity. The cross-section of a separately prepared sample was observed with a transmission type electron microscope, and found that the porous layer had a total thickness of about 1.5 μm and the portion of the porous layer of from the surface to a depth of about 150 nm had a coarse structure. This coarse structure is considered to be formed from high-concentration boron-doped Si layer by porous structure formation. The multilayer region of Si/SiGe quantum well immediately below the coarse portion are equally of a superfine structure, and the difference of the structure caused by the difference of the composition was not detected because of the extreme thinness of the respective layers. The superfine structure portion is considered to be supported by the coarse structure layer on the surface without spontaneous collapse.

Then, an aluminum electrode was formed in a shape of a comb on the front face of the wafer.

With the element prepared above, DC current was made to flow between the electrode on the front and back faces of the wafer, whereby visible light was emitted at a room temperature in the current direction where the electrode on the front face was used as the anode. The spectrum of the emitted light had a distinct peak at about 650 nm, and the emitted light was highly monochromatic. This is presumably due to the fact below. The superfine porous structure was given to the two-dimensional quantum well structure of the original multi-layered film prior to porous structure formation, thereby attaining a three-dimensional quantum well structure having relatively uniform enclosure size. Consequently, in a non-porous multilayered film, the wavelength of the peak of the emitted light which was at the longer wavelength side than the more highly monochromatic light shifted to the shorter wavelength side, while in the porous film of Si or SiGe which is not of a multi-layered structure, the broad spectrum of the visible light emitted at a room temperature became sharp.

In such a manner, a plurality of the porous layers of the element coexist to perform a plurality of functions without impairing the functions of the respective layers, thereby achieving the second object of the present invention. Further, the first object of the present invention is simultaneously achieved in that the porous layer of the coarse structure at the outermost layer mechanically supports the layer at the under portion having a brittle superfine structure to achieve structural stability of the element.

EXAMPLE 5

A light-emitting element was prepared by employing porous silicon and gallium-aluminum-arsine.

A monocrystalline silicon substrate of plane orientation [100] doped with boron having resistivity of 10 Ω·cm was prepared. To the back face of the substrate, boron ions accelerated to 50 keV were implanted at a dose of $5 \times 10^{14}$ cm$^{-2}$ and activated by thermal annealing in a nitrogen atmosphere at 950° C. for 30 minutes. On the front face of the wafer, a gallium-aluminum-arsine layer of 1 μm thick was formed by an MBE process, and further thereon a silicon layer doped with high concentration of arsine was epitaxially grown to a thickness of 200 nm by bias sputtering to obtain a supporting substrate and non-porous starting material.

Then anodization was conducted in the same manner as in Example 1 except that the concentration of the hydrofluoric acid in the etching solution was 25%, the current density was 10 mA·cm$^{-2}$, and the anodization time was 10 minutes.

The surface of the resulting anodized silicon wafer was kept in a mirror-polished state without formation of a crack or other defect, but the surface was observed to have discolored owing to the formation of porosity. The cross-section of the sample was observed by electron microscopy, and it was noted that a multi-layer structure was formed in which the outermost silicon layer had a coarse structure, the directly under gallium-aluminum-arsine layer had a superfine structure, and the region anodized to the silicon substrate had a superfine structure. At least, the outermost layer of the coarse structure surely gave additional structural strength to the superfine porous layer to stabilize it. Practically, aluminum in the gallium-aluminum-arsine layer is damaged by hydrofluoric acid, and the anodization of gallium-arsine gives only a brittle porous matter. Therefore, a sample which had been anodized without preliminary formation of an outermost silicon layer could not be used for subsequent process such as electrode formation.

Finally, on each face of the wafer, the electrode was formed in the same manner as in Example 1.

DC current was made to flow between the electrodes of the element, and the edge face of the lamination structure was observed. Thereby light was found to be emitted from the gallium-aluminum-arsine layer having a superfine porous structure. The intensity of the emitted light was about ten times that of the non-porous gallium-aluminum-arsine, and the peak wavelength shifted by about 100 nm to the high energy side. These results are considered to result from a kind of multiple quantum well structure formed by porous structure formation of a superfine structure of gallium-aluminum-arsine.

As described above, the semiconductor device of the present invention has a plurality of porous regions having different structures or compositions: some porous region has fine structure performing the main function of the device, and another porous region has a coarse structure having sufficient strength to support the fine porous region structurally. Thereby, a semiconductor device is provided which employs porous functional material having practicably sufficient strength without impairing the intended function.

The process of the present invention produces a semiconductor device having a plurality of porous regions having different structures or compositions readily with sufficient controlability by modifying partially a non-porous material and subsequently making the material porous, or by changing the treating conditions for porous structure formation, or by a like method.

What is claimed is:

1. A process for producing a semiconductor device comprising:

providing a non-porous substrate; and anodizing the non-porous substrate while changing electric current density to form the semiconductor device, which includes a non-porous substrate region and a plurality of porous regions having structures different from each other;

wherein a first porous region has a brittle structure;

wherein a second porous region has a strong structure; and wherein the first porous region is sandwiched between the second porous region and the non-porous substrate region.

2. The process according to claim 1, wherein the electric current density is increased or decreased, in any order.

3. The process according to claim 1, wherein the electric current density is increased stepwise.

4. The process according to claim 1, wherein the anodization is conducted in a solution containing hydrofluoric acid.

5. The process according to claim 1, wherein the non-porous substrate comprises a non-porous monocrystalline semiconductor.

6. The process according to claim 5, wherein the non-porous substrate comprises non-porous monocrystalline silicon.

7. The process according to claim 1 further comprising the step of forming a metallic film on the entire surface of the non-porous substrate prior to the anodization, wherein an anode is disposed opposite to the non-porous substrate and current is passed between the anode and the metallic film as a cathode to conduct the anodization.

* * * * *

UNITED STATES PATENT AND TRADEMARK OFFICE
CERTIFICATE OF CORRECTION

PATENT NO.   : 5,970,361
DATED        : October 19, 1999
INVENTOR(S)  : HIDEYA KUMOMI ET AL.

It is certified that error appears in the above-identified patent and that said Letters Patent is hereby corrected as shown below:

ON THE TITLE PAGE [56] References Cited:

FOREIGN PATENT DOCUMENTS, "57103243 6/1982 Japan" should
        read --57-103243 6/1982 Japan--; and
    OTHER PUBLICATIONS, in "T. Unagami et al.;", "Socitey,"
        should read --Society,--.

COLUMN 2:

Line 39, "FIG. 1" should read --FIGS. 1A and 1B--.

COLUMN 3:

Line 36, "FIG. 1" should read --FIG. 1A--;
    Line 39, "FIG. 1," should read --FIG. 1A,--;
    Line 52, "the" (second occurrence) should be deleted;
        and
    Line 55, "FIG. 1" should read --FIG. 1B--.

COLUMN 4:

Line 15, "a" should be deleted.

COLUMN 7:

Line 54, "the" (first occurrence) should be deleted; and
    Line 57, "the" (second occurrence) should be deleted.

COLUMN 8:

Line 38, "the" (first occurrence) should be deleted; and
    Line 46, "electric-current" should read --electric
        current--.

UNITED STATES PATENT AND TRADEMARK OFFICE
CERTIFICATE OF CORRECTION

PATENT NO. : 5,970,361
DATED : October 19, 1999
INVENTOR(S) : HIDEYA KUMOMI ET AL.

It is certified that error appears in the above-identified patent and that said Letters Patent is hereby corrected as shown below:

COLUMN 9:

Line 12, "prepared." should read --was prepared.--; and
    Line 19, "Initially" should read --Initially,--.

COLUMN 11:

Line 11, "controlability" should read
        --controllability--; and
    Line 14, "like" should read --similar--.

COLUMN 12:

Line 19, "claim 1" should read --claim 1,--.

Signed and Sealed this

Seventh Day of November, 2000

Attest:

Q. TODD DICKINSON

*Attesting Officer*     *Director of Patents and Trademarks*